United States Patent
Bank et al.

[11] Patent Number: 6,087,523
[45] Date of Patent: Jul. 11, 2000

[54] PLATINUM CATALYST FOR HYDROSILATIONS

[75] Inventors: Howard Marvin Bank, Freeland; Paul Charles Dinh; Ming-Shin Tzou, both of Midland, all of Mich.

[73] Assignee: Dow Corning Corporation, Midland, Mich.

[21] Appl. No.: 09/359,404

[22] Filed: Jul. 23, 1999

[51] Int. Cl.$^7$ .................................................... C07F 7/08
[52] U.S. Cl. ............................................................ 556/479
[58] Field of Search ............................................. 556/479

[56] References Cited

U.S. PATENT DOCUMENTS

| | | | |
|---|---|---|---|
| 2,823,218 | 2/1958 | Speier et al. | 260/448.2 |
| 2,851,473 | 9/1958 | Wagner et al. | 260/448.2 |
| 3,220,972 | 11/1965 | Lamoreaux | 260/46.5 |
| 4,064,154 | 12/1977 | Chandra et al. | 556/410 |
| 4,503,160 | 3/1985 | Williams, Jr. | 502/158 |
| 4,578,497 | 3/1986 | Onopchenko et al. | 556/479 |
| 5,041,595 | 8/1991 | Yang et al. | 556/479 |
| 5,206,402 | 4/1993 | McVannel et al. | 556/479 |
| 5,359,111 | 10/1994 | Kleyer et al. | 556/479 |
| 5,578,692 | 11/1996 | Biggs et al. | 528/15 |

FOREIGN PATENT DOCUMENTS 0 533 170 A1  3/1993  European Pat. Off. .

*Primary Examiner*—Paul F. Shaver
*Attorney, Agent, or Firm*—Melvin D. Fletcher

[57] ABSTRACT

A hydrosilation process comprising contacting a silicon hydride with an unsaturated reactant in the presence of a platinum catalyst supported on porous aluminum oxide having an acidity of pH 2 to 7. The process is particularly useful for the hydrosilation of unsaturated reactants where the unsaturation is in the internal portion of the reactant's structure, for example, as in cyclopentene and cyclohexene.

23 Claims, No Drawings

PLATINUM CATALYST FOR HYDROSILATIONS

BACKGROUND OF THE INVENTION

The present invention is a hydrosilation process comprising contacting a silicon hydride with an unsaturated reactant in the presence of a platinum catalyst supported on porous aluminum oxide having an acidity of pH 2 to 7. The process is particularly useful for the hydrosilation of unsaturated reactants where the unsaturation is in the internal portion of the reactant's structure, for example, as in cyclopentene and cyclohexene.

It is known in the art to produce organosilicon compounds by reacting a silicon hydride containing compound with an unsaturated organic compound in the presence of a catalyst. This reaction is commonly referred to as hydrosilation or hydrosilylation. Typically the catalyst is platinum metal on a carbon support, a platinum compound generally in a solvent, or a platinum complex.

Speier et al., U.S. Pat. No. 2,823,218, teaches a method for the production of organosilicon compounds by reacting Si-H with a compound containing aliphatic carbon atoms linked by multiple bonds in the presence of chloroplatinic acid. Lamoreaux, U.S. Pat. No. 3,220,972, teaches a similar process, however the catalyst is a reaction product of chloroplatinic acid.

Wagner et al., U.S. Pat. No. 2,851,473, disclose a process for the production of organosilicon compounds comprising reacting an unsaturated organic compound with a platinum-gamma alumina catalyst.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teaches the use of an oxygenated platinum containing catalyst for use in hydrosilating alkylsilanes. Kleyer et al., EP Patent Application No. 0533170A1, discloses a method for controlling a hydrosilation reaction by controlling the solution concentration of oxygen in the reaction mixture, relative to the platinum present in the reaction mixture.

In addition to the problem of de-activation of the platinum catalyst, hydrosilation processes taught in the art are not particularly effective in hydrosilating internal unsaturated bonds in organic molecules.

SUMMARY OF INVENTION

The present invention is a hydrosilation process comprising contacting a silicon hydride with an unsaturated reactant in the presence of a platinum catalyst supported on aluminum oxide. The process is particularly useful for hydrosilating cyclic olefines such as cyclopentene and cyclohexene.

DETAILED DESCRIPTION OF INVENTION

The present invention is a hydrosilation process comprising contacting a silicon hydride with an unsaturated reactant in the presence of a platinum catalyst supported on porous aluminum oxide having an acidity of pH 2 to 7. The hydrosilation process comprises:

(A) contacting a silicon hydride described by formula $R^1_a H_b SiX_{4-a-b}$ where each $R^1$ is independently selected from the group consisting of alkyls comprising one to about 20 carbon atoms, cycloalkyls comprising about four to about 12 carbon atoms, and aryls; each X is a halogen; a=0 to 3, b=1 to 3, and a+b=1 to 4; and (B) an unsaturated reactant selected from the group consisting of
   (i) substituted and unsubstituted unsaturated hydrocarbon compounds,
   (ii) silicon compounds comprising substituted or unsubstituted unsaturated hydrocarbon substituents, and
   (iii) mixtures of (i) and (ii);

in the presence of a hydrosilation catalyst comprising 0.1 to about 15 weight percent platinum supported on porous aluminum oxide having an acidity of pH 2 to 7.

The contacting of the silicon hydride with the unsaturated reactant can be effected in standard reactors for conducting hydrosilation processes. The process may be run as a continuous, semi-continuous, or batch process.

Silicon hydrides useful in the present process are described by formula $R^1_a H_b SiX_{4-a-b}$ where each $R^1$ is independently selected from the group consisting of alkyls comprising one to 20 carbon atoms, cycloalkyls comprising four to 12 carbon atoms, and aryls; a=0 to 3, b=1 to 3, and a+b=1 to 4. $R^1$ can be a substituted or unsubstituted alkyl, cycloalkyl, or aryl as described. It is preferred that each $R^1$ be independently selected from a group consisting of alkyls comprising one to about six carbon atoms. Even more preferred is when each $R^1$ is methyl. Each X is an independently selected halogen radical and preferably X is chlorine. Examples, of silicon hydrides described by formula $R^1_a H_b SiX_{4-a-b}$ which may be useful in the present process include trimethylsilane, dimethylsilane, triethylsilane, dichlorosilane, trichlorosilane, methyldichlorosilane, dimethylchlorosilane, ethyldichlorosilane, cyclopentlydichlorosilane, methylphenylchlorosilane and (3,3,3-trifluoropropyl)dichlorosilane. Preferably, the silicon hydride is selected from a group consisting of methyldichlorosilane and dichlorosilane.

The silicon hydride is contacted with an unsaturated reactant selected from a group consisting of (i) substituted and unsubstituted unsaturated hydrocarbon compounds, (ii) silicon compounds comprising substituted and unsubstituted unsaturated hydrocarbon substituents, and (iii) mixtures of (i) and (ii). For purpose of this invention, "unsaturated" means that the compound contains at least one carbon—carbon double bond.

More specific examples of the unsaturated reactants useful in the process include unsubstituted cycloalkene compounds comprising at least four carbon atoms, substituted cycloalkene compounds comprising at least four carbon atoms, linear alkene compounds comprising two to about 30 carbon atoms, branched alkene compounds comprising four to about 30 carbon atoms, and mixtures of two or more of any of the above.

The substituted and unsubstituted cycloalkene compounds useful in the process are those containing one or more unsaturated carbon—carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated hydrocarbon compounds useful in the process are linear and branched alkene compounds including, for example, compounds with terminal unsaturation such as 1-hexene and 1,5-hexadiene, compounds with internal unsaturation such as trans-2-hexene, and unsaturated aryl containing compounds such as styrene and alpha-methylstyrene.

The unsaturated reactants may also comprise halogen, oxygen in the form of acids, anhydrides, esters, and ethers, and nitrogen. Two or more of the above described unsaturated hydrocarbon compounds may be used in the present process.

The unsaturated hydrocarbon compounds comprising halogen may include, for example, vinyl chloride, allyl chloride, allyl bromide, allyl iodide, allyl bromide, methallyl chloride, trichloroethylene, tetrachloroethylene, tetrafluoroethylene, chloroprene, vinyldiene chloride, and dichlorostyrene.

Suitable unsaturated hydrocarbon compounds comprising oxygen can include, for example, ethers such as allyl and vinyl ethers; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated hydrocarbon compounds include, for example, indigo, indole, acrylonitrile, and allyl cyanide.

Specifically included within the definition of unsaturated hydrocarbon compounds are those substituted by organo-functional moieties such as

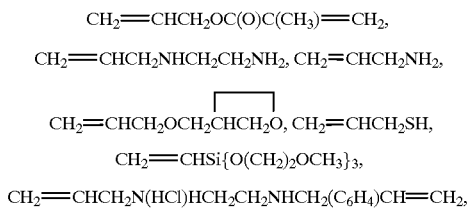

and other similar such compounds.

The unsaturated hydrocarbon compound can be a silicon compound comprising substituted and unsubstituted hydrocarbon substituents as described by, for example, formulas $(CH_2=CH(CH_2)_g)_h R^1_i Si(OR^1)_{4-h-i}$ and $(CH_2=CH(CH_2)_g)_h R^1_i SiCl_{4-h-i}$, where $R^1$ is as previously described, g=0 to 12, h=1 to 3, i=0 to 3, and h+i=1 to 4.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated alumina or molecular sieves.

The relative amounts of silicon hydride and unsaturated reactant used in the present process can be varied within wide limits. Although one unsaturated carbon—carbon linkage per silicon bonded hydrogen atom is stoichiometric, there is no requirement that the process be run under stoichiometric conditions. Generally, it is preferred that the process be run with a stoichiometric excess of silicon hydride. Preferred is when the process is run with about 0.1 to 10 percent stoichiometric excess of silicon hydride.

The silicon hydride and unsaturated reactant are contacted in the presence of a platinum catalyst supported on porous aluminum oxide having an acidity of pH 2 to 7. The platinum can be supported on the aluminum oxide using methods known in the art, such as wet impregnation.

Suitable platinum compounds for supporting on aluminum oxide are described, for example, in Onopchenko et al., U.S. Pat. No. 4,578,497; Lamoreaux, U.S. Pat. No. 3,220,972 and Speier, U.S. Pat. No. 2,823,218, all of which are hereby incorporated herein by reference. The platinum can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)-platinum(II), cis-dichlorobis(acetonitrile)-platinum(II), dicabonyldichloroplatinum(II), platinum chloride, and platinum oxide. A preferred platinum is selected from the group consisting of chloroplatinic acid, chloroplatinic acid hexahydrate, and platinum vinylsiloxane complexes such as a neutralized complex of chloroplatinic acid with sym-divinyltetramethyldisiloxane.

The catalyst useful in the present process has about 0.1 to 15 weight percent platinum supported on porous aluminum oxide having an acidity of pH 2 to 7. Preferably the porous aluminum oxide has about 0.4 to 5 weight percent platinum supported thereon. Most preferably the porous aluminum oxide has about 0.5 weight percent platinum supported thereon and an acidity of pH 4 to 6. An acid such as hydrogen chloride may be added to the platinum supported on porous aluminum oxide catalyst to adjust the acidity within the range of pH 2 to 7. The acidity of the catalyst can be determined by conventional titration methods using a base and indicator.

The porous aluminum oxide support utilized in the present process has a BET surface area of at least about 75 to 350 m$^2$/g. Preferably, the BET surface area is about 100 to 200 m$^2$/g. Most preferable, the porous aluminum oxide support is spherical and has a diameter of about one to 11 mm and preferably a diameter of about 2 to 6 mm. The porous aluminum oxide support can have an average pore diameter of about 200 to 10,000 nm. It is preferred that the porous aluminum oxide support have an average pore diameter of about 5 to 30 nm.

The concentration of the platinum catalyst supported on porous aluminum oxide added to the present process may vary within a wide limit. Concentrations of one mole of platinum metal per billion moles of unsaturated carbon—carbon bonds added to the process by the unsaturated reactant may be useful in the present process. Concentrations as high as one mole of platinum metal per one thousand moles of unsaturated carbon—carbon bonds added to the process by the unsaturated reactant may be useful. Higher concentrations of platinum may be used if desired. A preferred concentration of platinum catalyst supported on porous aluminum oxide is one providing about one to 1000 moles of platinum metal per 1×10$^3$ moles of unsaturated carbon—carbon bonds provided to the process by the unsaturated reactant.

The catalyst may be premixed in a solvent for ease of handling. Suitable solvents include, for example, non-polar hydrocarbon solvents such as benzene, toluene, and xylene and polar solvents such as glycols, and esters.

The following examples are provided to illustrate the present invention. These examples are not intended to limit the claims herein.

EXAMPLE 1

Evaluation to produce cyclohexylmethyldichlorosilane by contacting cyclohexene with methyldichlorosilane in the presence of 0.5%-Pt/Al$_2$O$_3$ catalyst. All experiments were conducted in a 1 liter continuous stirred-tank reactor (CSTR) equipped with a cooling coil, heating mantle, thermocouple and temperature controller. The CSTR was loaded with 86.7 gms of porous spherical 0.5%-Pt/Al$_2$O$_3$ catalyst having an acidity of pH 6 purchased from Engelhard Corporation, Iselin, N.J. The catalyst was dried with nitrogen gas at a flow rate of 2 liters/m at 140° C. for 6 hours. Methyldichlorosilane (330 gm/hr, 2.86 gmol/hr) and cyclohexene (150 gm/hr, 1.83 gmol/hr) were fed into the CSTR and the temperature maintained at 100° C.±1° C. The cyclohexylmethyldichlorosilane product from the CSTR was analyzed by gas chromatography (GC) using a thermal conductivity detector (TCD) for cyclohexylmethyldichlorosilane. The experiment was repeated using the same procedure at 120° C. and 140° C. The reaction temperature, contact time, percent conversion and reaction rate are reported in Table 1.

EXAMPLE 2

Evaluation to produce cyclohexylmethyldichlorosilane by contacting cyclohexene with methyldichlorosilane in the presence of porous spherical 0.5%-Pt/Al$_2$O$_3$ catalyst having an acidity within a range of pH 4 to 5. The CSTR was loaded with 86.7 gms of porous spherical 0.5%-Pt/Al$_2$O$_3$ catalyst having an acidity of pH 4 to 5 purchased from Johnson Matthey, West Deptford, N.J. The catalyst was dried with argon gas at a flow rate of 2 liters/m at 140° C. for 6 hours. Methyldichlorosilane (330 gm/hr, 2.86 gmol/hr) and cyclohexene (150 gm/hr, 1.83 gmol/hr) were fed into the CSTR and the temperature maintained at 120° C.±1° C. The cyclohexylmethyldichlorosilane product from the CSTR was analyzed by gas chromatography (GC) using a thermal conductivity detector (TCD) for cyclohexylmethyldichlorosilane. The reaction temperature, contact time, percent conversion and reaction rate are reported in Table 1.

EXAMPLE 3

Evaluation to produce cyclopentylmethyldichlorosilane by contacting cyclopentene with methyldichlorosilane in the presence of porous spherical 0.5%-Pt/Al$_2$O$_3$ catalyst having an acidity within a range of pH 4 to 5. The CSTR was loaded with 86.7 gms of porous spherical 0.5%-Pt/Al$_2$O$_3$ catalyst having an acidity within a range of pH 4 to 5 purchased from Johnson Matthey, West Deptford, N.J. The catalyst was dried with argon gas at a flow rate of 2 liters/m at 140° C. for 6 hours. Methyldichlorosilane (330 gm/hr, 2.86 gmol/hr) and cyclopentene (150 gm/hr, 2.20 gmol/hr) were fed into the CSTR and the temperature maintained at 120° C.±1° C. The cyclopentylmethyldichlorosilane product from the CSTR was analyzed by gas chromatography (GC) using a thermal conductivity detector (TCD) for cyclopentylmethyldichlorosilane. The reaction temperature, contact time, percent conversion and reaction rate are reported in Table 1.

EXAMPLE 4

Evaluation to produce cyclopentylmethyldichlorosilane by contacting cyclopentene with methyldichlorosilane in the presence of porous 0.5%-Pt/C catalyst. The CSTR was loaded with 86.7 gms of porous 0.5%-Pt/C catalyst. The catalyst was dried with nitrogen gas at a flow rate of 2 liters/m at 140° C. for 6 hours. Methyldichlorosilane (330 gm/hr, 2.86 gmol/hr) cyclopentene(150 gm/hr, 1.83 gmol/hr) were fed into the CSTR and the temperature maintained at 100° C.±1° C. The cyclopentylmethyldichlorosilane product from the CSTR was analyzed by gas chromatography (GC) using a thermal conductivity detector (TCD) for cyclopentylmethyldichlorosilane. The experiment was repeated at 150° C. using the same procedure. The reaction temperature, contact time, percent conversion and reaction rate are reported in Table 1.

TABLE 1

| Example No. | Temp. ° C. | Contact Time Min. | % Conversion | Reaction Rate Mol/Hr/Gm Cat. |
|---|---|---|---|---|
| 1 | 100 | 10.8 | 28 | 0.004 |
| 1 | 120 | 10.8 | 29 | 0.006 |
| 1 | 140 | 10.8 | 33 | 0.008 |
| 2 | 120 | 10.8 | 65 | 0.011 |
| 3 | 120 | 10.8 | 70 | 0.016 |
| 4 | 100 | 10.8 | <2 | — |
| 4 | 150 | 10.8 | <2 | — |

We claim:
1. A hydrosilation process comprising:
   (A) contacting a silicon hydride described by formula $R^1_a H_b SiX_{4-a-b}$ where each $R^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and
   (B) an unsaturated reactant selected from the group consisting of
      (i) substituted and unsubstituted unsaturated hydrocarbon compounds,
      (ii) silicon compounds comprising substituted or unsubstituted unsaturated hydrocarbon substituents, and
      (iii) mixtures of (i) and (ii);
in the presence of a hydrosilation catalyst comprising about 0.1 to 15 weight percent platinum catalyst supported on porous aluminum oxide having an acidity of pH 2 to 7.

2. A process according to claim 1, where the hydrosilation catalyst comprises about 0.4 to 5 weight percent platinum catalyst supported on porous aluminum oxide having an acidity of pH 2 to 7.

3. A process according to claim 1, where the hydrosilation catalyst comprises about 0.5 weight percent platinum catalyst supported on porous aluminum oxide having an acidity of pH 2 to 7.

4. A process according to claim 1, where the silicon hydride is selected from the group consisting of methyldichlorosilane and dichlorosilane.

5. A process according to claim 1, where the unsaturated reactant is cyclopentene.

6. A process according to claim 1, where the unsaturated reactant is cyclohexene.

7. A process according to claim 1, where the platinum is selected from the group consisting of chloroplatinic acid, chloroplatinic acid hexahydrate, and platinum vinylsiloxane complexes.

8. A process according to claim 1, where the silicon hydride is dichlorosilane and the unsaturated reactant is cyclohexene.

9. A process according to claim 1, where the silicon hydride is dichlorosilane and the unsaturated reactant is cyclopentene.

10. A process according to claim 1, where the silicon hydride is methyldichlorosilane and the unsaturated reactant is cyclohexene.

11. A process according to claim 1, where the silicon hydride is methyldichlorosilane and the unsaturated reactant is cyclopentene.

12. A process according to claim 1, where the process is conducted with about 0.1 to 10 percent stoichiometric excess of silicon hydride in relation to the unsaturated carbon—carbon bonds of the unsaturated reactant.

13. A process according to claim 1, where the hydrosilation catalyst present is about one to 1000 moles of platinum metal bonded to the porous aluminum oxide per $1 \times 10^3$ moles of unsaturated carbon—carbon bonds provided to the process by the unsaturated reactant.

14. A process according to claim 1, where the hydrosilation catalyst comprises porous aluminum oxide spheres having a diameter of about one to 11 mm.

15. A process according to claim 1, where the hydrosilation catalyst comprises porous aluminum oxide spheres having a diameter of about 2 to 6 mm.

16. A process according to claim 14, where the spheres have an average pore diameter of about 200 to 10,000 nm.

17. A process according to claim 14, where the spheres have an average pore diameter of about 5 to 30 nm.

18. A process according to claim 1, where the porous aluminum oxide has a BET surface area of at least about 75 to 350 $m^2/g$.

19. A process according to claim 1, where the porous aluminum oxide has a BET surface area of at least about 100 to 200 $m^2/g$.

20. A process according to claim 1, where the porous aluminum oxide has an acidity of pH 4 to 6.

21. A hydrosilation process comprising:

contacting a silicon hydride described by formula $R^1{}_aH_bSiX_{4-a-b}$ where each $R^1$ is independently selected from the group consisting of alkyls comprising one to about 20 carbon atoms, cycloalkyls comprising about four to 12 carbon atoms, and aryls; each X is a halogen; a=0 to 3, b=1 to 3, and a+b=1 to 4; and cyclohexene or cyclopentene in the presence of a hydrosilation catalyst comprising 0.1 to about 15 weight percent platinum catalyst supported on porous aluminum oxide having an acidity of pH 2 to 7.

22. A process according to claim 21, where the hydrosilation catalyst comprises about 0.5 weight percent platinum catalyst supported on porous aluminum oxide having an acidity of pH 2 to 7.

23. A process according to claim 22, where the porous aluminum oxide has an acidity of pH 4 to 6.

* * * * *